(12) United States Patent
Abramson

(10) Patent No.: US 7,156,847 B2
(45) Date of Patent: Jan. 2, 2007

(54) APPARATUS FOR THE CORRECTION OF CHEST WALL DEFORMITIES SUCH AS PECTUS CARINATUM AND METHOD OF USING THE SAME

(76) Inventor: Horacio Abramson, Libertador 1688, Vicente Lopez, Buenos Aires (AR) 1638

( * ) Notice: Subject to any disclaimer, the term of this patent is extended or adjusted under 35 U.S.C. 154(b) by 443 days.

(21) Appl. No.: 10/663,580

(22) Filed: Sep. 16, 2003

(65) Prior Publication Data
US 2004/0117016 A1    Jun. 17, 2004

(30) Foreign Application Priority Data
Nov. 6, 2002    (AR) .............................. P020104229

(51) Int. Cl.
*A61B 17/56*    (2006.01)
(52) U.S. Cl. .......................... 606/60; 606/71
(58) Field of Classification Search ................. 606/60, 606/69, 70, 71; 623/16.11, 23.47
See application file for complete search history.

(56) References Cited

U.S. PATENT DOCUMENTS

| | | | | |
|---|---|---|---|---|
| 5,092,893 | A | * | 3/1992 | Smith .......................... 606/61 |
| 5,665,089 | A | * | 9/1997 | Dall et al. .................... 606/71 |
| 6,024,759 | A | | 2/2000 | Nuss et al. |
| 2003/0036759 | A1 | * | 2/2003 | Musso ......................... 606/69 |

OTHER PUBLICATIONS

"Surgical Correction of Pectus Excavatum", Shamberger et al., Journal of Pediatric Surgery, 22, Jan. 1987, pp. 48-53.

"Pectus Carinatum", Robicsek et al., J. Thoracic and Cardiovascular. Surgery, 1979, 78: pp. 52-61.

"The Operative Correction of Pectus Carcinatum (pigeon breast)", Ravitch MD. Annals of Surgery, May 1960, 151, pp. 705-714.

"A 10-year Review of Minimally Invasive Technique for the Correction of Pectus Excavatum". Nuss et al. J. of Pediatric Surgery 33, 4, Apr. 1998, pp. 545-522.

"Experience and Modification Update for the Minimally Invasive Nuss Technique for Pectus Excavatum Repair in 303 Patients". J. of Pediatric Surgery 37, 3, Mar. 2002, pp. 437-445.

* cited by examiner

*Primary Examiner*—Eduardo C. Robert
*Assistant Examiner*—James L. Swiger
(74) *Attorney, Agent, or Firm*—Pearne & Gordon LLP

(57) ABSTRACT

An apparatus for the correction of wall chest deformities, such as "Pectus Carinatum", comprising: a bar (10) having a flattened cross-section, having a minimum bending strength according to the values defined by ASTM F382-95, plates (20) having a slot (21) in the medium portion so as to fit the corresponding end of the bar (10) and peripheral holes (23) for securing the bone parts. The bar ends comprise planar grooves (11–11') determining the wall thickness substantially similar to the height of the slot (21) of the plate (20). The wall of the grooves (11–11') has aligned holes (13) in order to form with the respective plate (20) and by using screws (30), a fixed removable attachment that allows the axial registration of the bar (10). Method for the correction of Pectus Carinatum using said apparatus in order to achieve a normal anatomic shape of the chest wall.

9 Claims, 5 Drawing Sheets

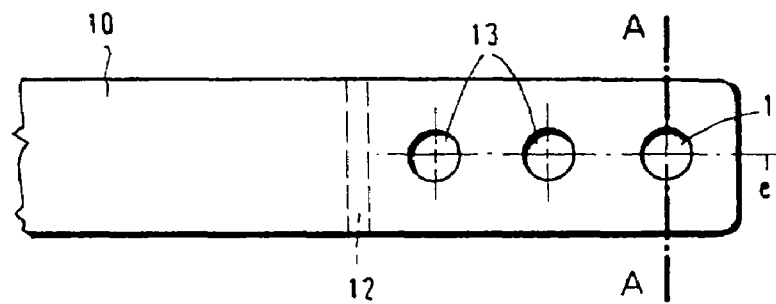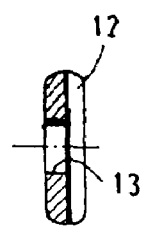
FIG.2A  FIG.2C
FIG.2B
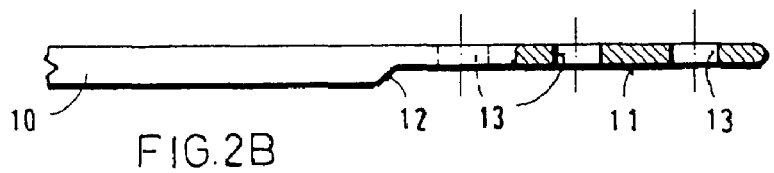
FIG.3A
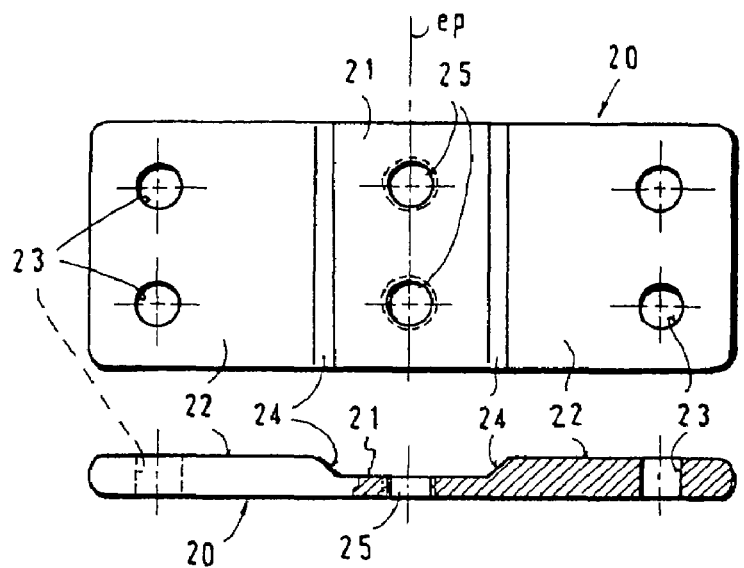
FIG.3B
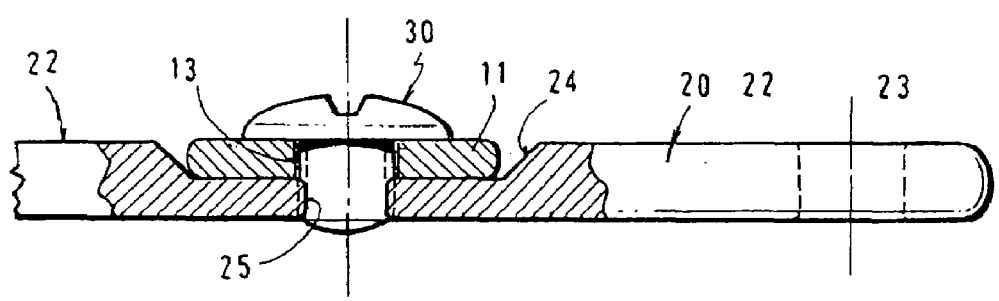
FIG.4

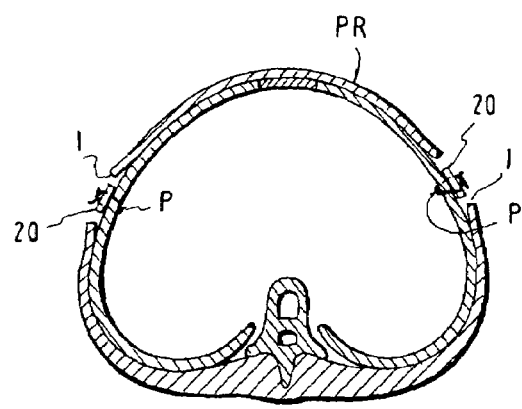
FIG. 8
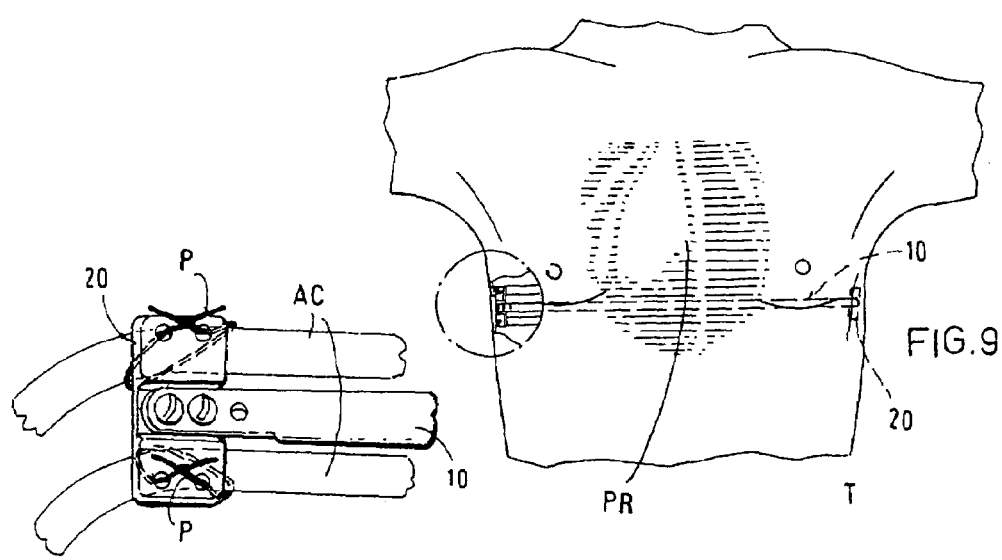
FIG. 10
FIG. 9
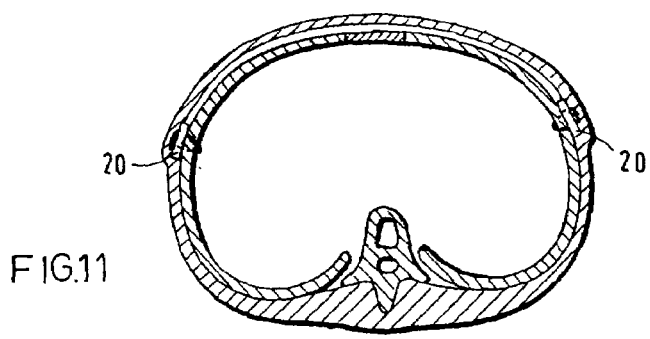
FIG. 11

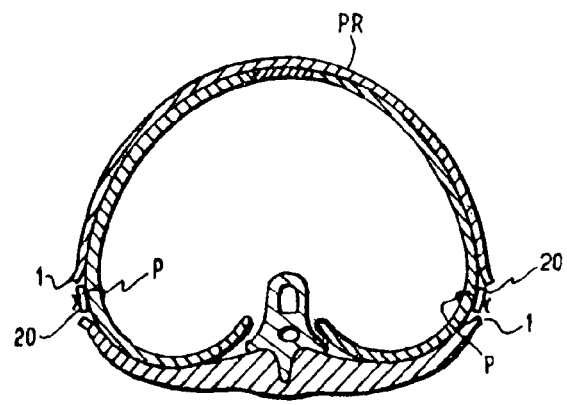
FIG. 12
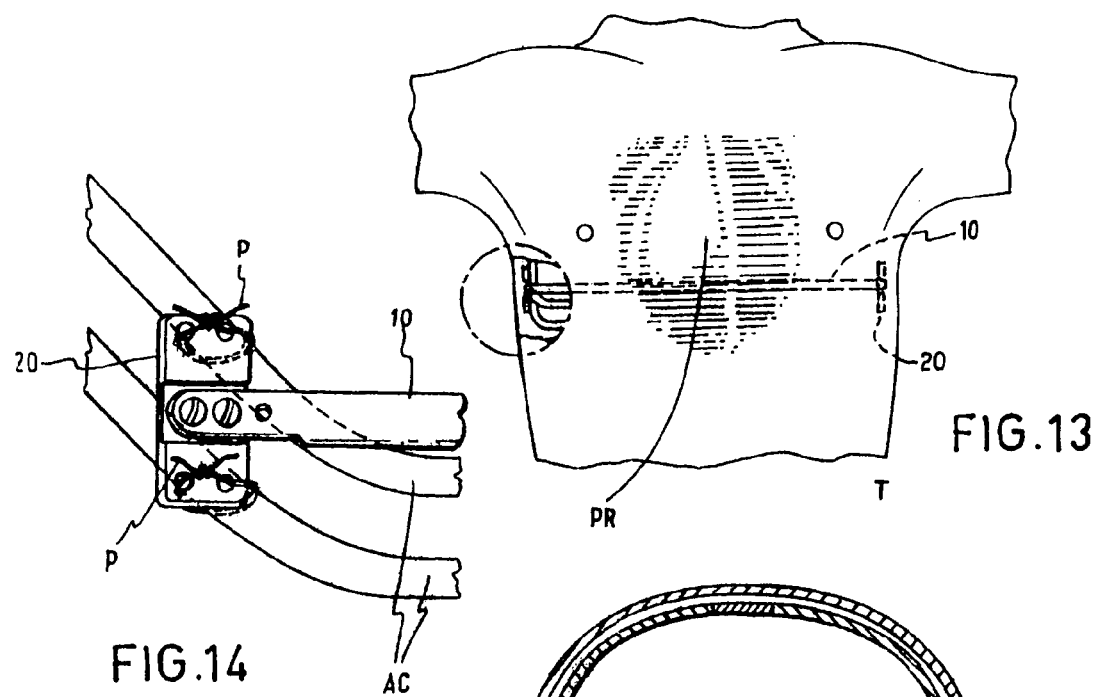
FIG. 13
FIG. 14
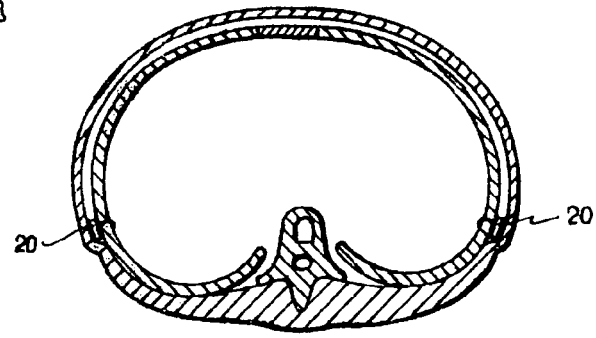
FIG. 15

APPARATUS FOR THE CORRECTION OF CHEST WALL DEFORMITIES SUCH AS PECTUS CARINATUM AND METHOD OF USING THE SAME

TECHNICAL FIELD

This invention relates generally to surgical apparatus for the correction of chest wall deformities, within the so-called minimally invasive surgeries, that correct the deformities without making rib, cartilage or sternum resection, i.e. avoiding hard, blood losing and disabling surgeries. Preferably, the wall chest deformity to be considered is Pectus Carinatum.

Even more precisely, this invention refers to an apparatus for the correction of wall chest deformities, such as Pectus Carinatum, as well as to a method for the correction of Pectus Carinatum.

SCOPE OF THE INVENTION

Discussion of the Related Art

Various modes of repair of congenital chest wall deformities (Pectus Excavatum and Pectus Carinatum) are currently known. The most universally accepted surgical methods are the Ravich technique with different variations and the Welsh technique. Both surgical procedures are invasive as they require large incisions and tissue movements: skin tissue, cell tissue, muscle tissue, and besides they require bone and cartilage tissue resection of the pathological rib portions. Finally, these procedures include sternum fracture in one or more portions, and securing thereof by placing or not a stabilizing element such as propylene mesh, metal bar, muscle flaps, and other procedures. These procedures are long and disabling and although they improve chest contour but, as they include chest wall resections they reduce the elasticity required for a correct expansion in inspiration-expiration and reduce chest wall size.

Some relevant references to the state of the art are as follows:
1) Surgical Correction of Pectus Excavatum by Robert C. Schamberger and Kenneth J. Welch, Boston, Mass. Published in Journal of Pediatric Surgery, Vol. 22, No. 1 (January), 1997; pp. 48–53.
2) Robicsek F, Cook J W, Daugherty, H K, et al: Pectus Carinatum. Published in J. Thorac. Cardiovasc. Surg., 1979, 78: 52–61.
3) Ravitch M M. The operative correction of Pectus Carinatum (pigeon breast). Published in Ann Surg 1960; 151: 705–14.

Referring to non-surgical treatment of Pectus Carinatum, orthesic methods with external compression systems have also been applied. These comprise the use during several years, especially during body growth period, of structures that are applied to the chest and apply pressure on the proceeding areas. The amount of pressure applied may vary. However, the development of these procedures has many difficulties. Long-term use is costly, complex and troublesome for patients. Although in some cases there have been good results, only partial improvements are usually found.

As regards the treatment of another chest wall deformity, Pectus Excavatum, U.S. Pat. No. 6,024,759 discloses a solution that comprises introducing an intrapleural bar (Pectus Bar) and inserting stabilizers placed at its ends. Rotating the bar advances the sternum depressed portion.

However, the securing system at its ends by fitting does not safely prevent detachment thereof. This system comprises an arcuate portion at both ends of the elongated bar which theoretically makes sliding of the stabilizers difficult. Currently and due to the high frequency of post-operative bar displacement it has become necessary to add steel wire clinching stitches wrapping both structures. This system, even with the addition of said clinching stitches, becomes extremely unreliable if subject to extreme forces tending to separate them. Besides and taking into account that the attachment of both elements is made by terminus-terminal fitting and that there is little space in the cell tissue pocket that is dissected in order to place the securing element at the end, its insertion becomes troublesome. For the same reasons, extraction thereof is made difficult, especially because the steel wire clinching stitches must be removed, obliging to bend the stabilizing bar so as to disengage it without cutting and removing said steel stitches.

Concretely, the forces applied on the correcting bar by the chest walls subject to correction in Pectus Excavatum tend to force the disengagement of the bar from its respective securing elements and cause said correcting bar to turn completely.

Some relevant references of the state of the art for the case of Pectus Excavatum are as follows:
1) A 10-Year Review of A Minimally Invasive Technique for the Correction of Pectus Excavatum. By Donald Nuss, Robert E. Kelly, Jr, Daniel P. Croitoru, and Michael E. Katz. Norfolk, Va., US. Published in Journal of Pediatric Surgery, Vol. 33, No. 4 (April), 1988; pp. 545–552.
2) Experience and Modification Update for the Minimally Invasive Nuss Technique for Pectus Excavatum Repair in 303 Patients. Published in Journal of Pediatric Surgery. Vol. 37, No. 3 (March), 2002; pp. 437–445.

SUMMARY AND OBJECT OF THE INVENTION

An apparatus for the correction of congenital wall chest deformities, such as "Pectus Carinatum" in its various types and variants, is proposed, comprising: a bar with a flattened cross-section, having a minimum bending strength according to the values determined by ASTM F-382-95, and fixation plates having a slot at the center portion so as to fit the end of the bar, and peripheral holes for fixation to bone parts. The bar ends comprise planar grooves defining a wall thickness substantially equal to the height of the plate slot. The groove wall has aligned holes in order to form the respective plate and by using screws, a removable fixed attachment allowing bar axial registration.

Another object of the present invention is a method for the correction of Pectus Carinatum using the above apparatus, wherein the bar of the apparatus acts as a compressor means and is previously convexly curved so that it may compress and suitably correct the proceeding, then it is introduced in front of the deformed sternum and cartilages, with the bar convexity resting on the anterior face of the sternum. Subsequently two bar stabilization and fixation plates are inserted in the lateral, preferably back axillary region of the chest, securing said plates to the costal arcs, preferably to two superior and inferior of them, through pericostal steel wire stitches and to the plate peripheral holes. The bar ends are mounted on the respective plate slots, matching two consecutive bar holes by chest compression and the two threaded holes of each plate, securing the joint with the screws, so that once fixed the bar shall apply the necessary pressure on the anterior sternochondral face in order to achieve a normal anatomic chest wall shape.

Later and in cases it is necessary, the compression of protruded region may be increased without removing the implant, by removing the screws and displacing the ends until two other consecutive holes match the plate holes, and securing the assembly with the same screws.

We are herein proposing a solution for the Pectus Carinatum problem by a novel intrathoracic compressive method that demands intensive pressures in order to satisfactorily compress back the proceeding sternum and ribs by taking a fixed point on the ribs in the axillary region, and thus the use of a fixing apparatus specially adapted for supporting such intensive forces.

This is achieved by using the correcting apparatus comprising holes separated by the same distance at the chest compressing bar ends, and wherein said ends have been designed by reducing their thickness so as to conform them to the respective fixing plates. As explained herein, each plate has a slot whereon the chest compressing bar is applied and wherein threaded holes are shown, separated by a distance consistent with the distances that separate the holes at the ends of the chest compressing bar and through which the securing screws are inserted, which provides a safe securing means that is easy to insert and remove. The new method also gives a better esthetic result as the added thickness of the bar ends and the plates is almost similar to that of each of them and unlike the fitting apparatus that triplicates said thickness, it is very well concealed in the subcutaneous cell tissue pocket in the axillary region.

Also, as discussed previously, according to the invention, both plates are firmly secured to the ribs by the steel wire stitches and on said plates the chest compressing bar is firmly secured by the screws passing through said chest compressing bar. Said screws are screwed in the threaded holes located in the slot of each fixing plate allowing to apply the necessary pressure to achieve the appropriate result on the chest contour and according to the progressive compression system of the novel method, it leaves the possibility of applying a greater pressure after a period of time ranging from three to nine weeks, by the simple procedure of reopening the small lateral incisions, removing the screw or screws, and applying a greater pressure and relocating them at a more advanced point, towards the chest compressing bar medial portion, thus reducing even more the sterno-vertebral space and increasing the chest wall volume in the lateral and basal region.

Other features of the object of the present invention will be explained in the description below.

BRIEF DESCRIPTION OF THE DRAWINGS

Taking into account the above and other related objects, the invention consists of the construction details and combination of parts based on the following description that refers to the attached drawings, wherein:

FIG. 2A is a partial plan view of an end of the bar comprising the above apparatus.

FIG. 2B is a lateral elevational and partially cross-sectional view of FIG. 2A.

FIG. 2C is a cross-sectional view of FIG. 2A taken along line A—A.

FIG. 3A is a plan view of a fixing plate corresponding to said bar end.

FIG. 3B is an elevational and partially cross-sectional view of said plate according to FIG. 3A.

FIG. 4 is a partial, larger scale, elevational and partially cross-sectional view of the mechanical attachment between said bar end and said plate.

FIG. 8 is cross-sectional schematic view of a human chest affected by a deformity such as "Pectus Carinatum", showing, according to the correction method of the invention, the lateral incisions for securing the bar fixation plates.

FIG. 9 is an elevational schematic view of the human chest showing, according to the correction method proposed, the insertion of compression bar and the fixation plates of said bar, including in an involving circle the attachment between one of the bar ends and one of the fixation plates.

FIG. 10 is a perspective view of said attachment between the bar end and the plate, showing the securing by pericostal steel wire stitches of the plate to bone parts of the costal arcs.

FIG. 11 is a cross-sectional schematic view of the human chest showing "Pectus Carinatum" type deformity in a corrected position according to the method of the invention.

FIG. 12 is a schematic cross-sectional view of a human chest affected by a deformity such as "Pectus Carinatum" showing, according to another embodiment of the correcting method of the invention, the lateral incisions in the posterior axillary region for securing the bar fixing plates.

FIG. 13 is a schematic elevational view of the human chest showing, according to another embodiment of the correcting method of the invention, the insertion of the compressing bar and the fixing plates of said bar in the posterior axillary region, including in an involving circle the attachment between one of the bar ends and one of the fixing plates.

FIG. 14 is a perspective view of said attachment between the bar end and the plate, showing another embodiment of the fixation by pericostal steel wire stitches of the plate to the bone parts of the costal arcs in the posterior axillary region.

FIG. 15 is a schematic cross-sectional view of the human chest showing the deformity such as "Pectus Carinatum" in the corrected position according to another embodiment of the method of the invention, wherein the fixation of the plate is made on the bone parts of the costal arcs in the posterior axillary region.

In said figures equal references indicate the same or corresponding parts.

LIST OF MAIN REFERENCE NUMBERS

Figure 1:
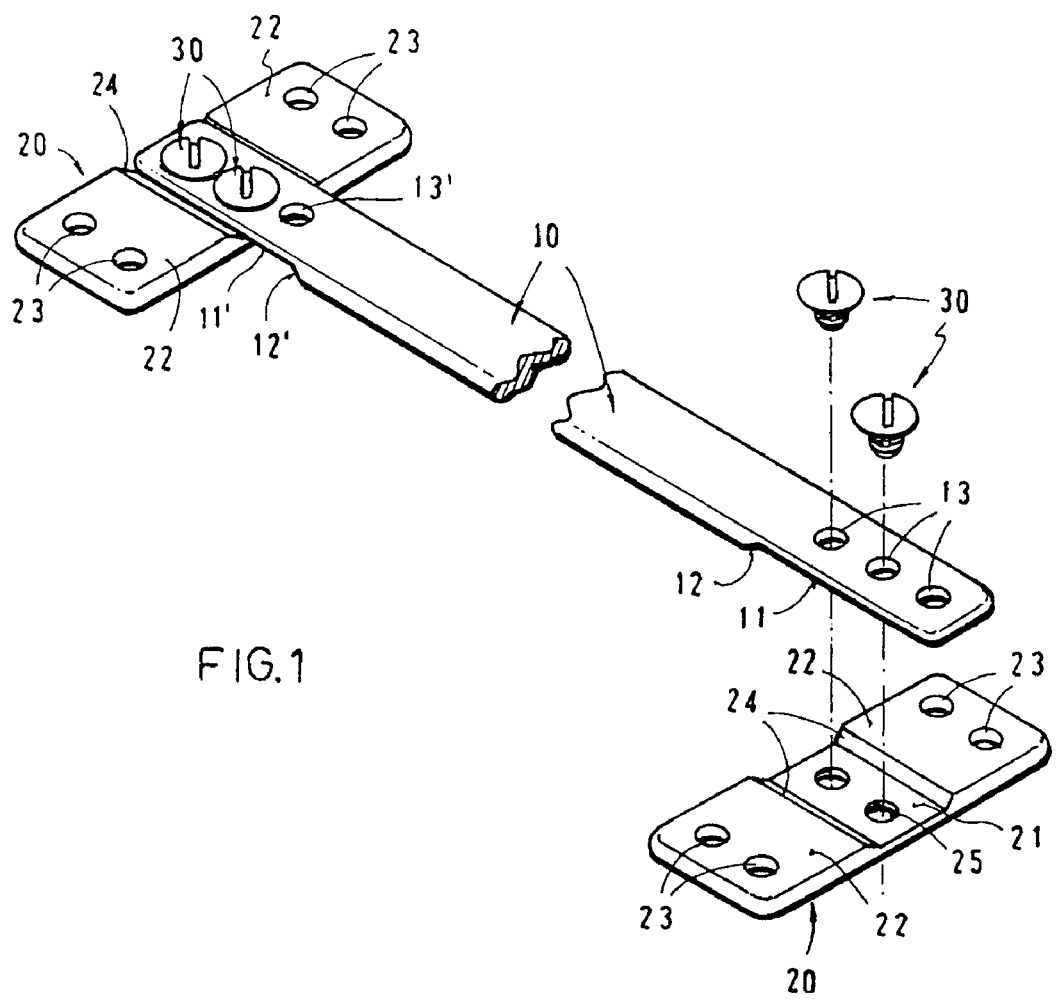
FIG. 1 is a perspective schematic view of a preferred embodiment of the inventive apparatus, for treating chest wall deformities, shown partially exploded.

(10) Pressing flexible bar
(11)(11') Planar grooves formed in the bar end portions (10).
(12)(12') Steps in transition chamfer between groove faces (11)(11') and one of the bar major faces (10).
(13)(13') Passing holes aligned with the longitudinal axis of grooves (11)(11')
(20) Rectangular plate for bar (10) fixation and stabilization
(21) Straight groove or slot formed in the medium cross-section portion of plate (20)
(22) Side portions of plate (20)
(23) Securing peripheral holes of plate (20)
(24) Steps in transition 45° chamfer between slot face (21) and side portions (22)
(25) Threaded holes aligned with the longitudinal axis of slot (21)

(20') Embodiment variation of Rectangular plate for bar (10) fixation and stabilization
(21') Straight groove or slot formed in the medium cross-section portion of plate (20')
(22') Side portions of plate (20')
(23') Securing peripheral holes of plate (20')
(24') Steps in transition 45° chamfer between slot face (21') and side portions (22')
(25') Threaded holes formed in side portions (22') adjacent to steps (24')
(26) Plate cylindrical projection
(30) Securing screws between bar ends (10) and plates (20)
(31) Head screws (30)
(eb) Longitudinal axis of grooves (11)(11')
(ep) Longitudinal axis of groove or slot (21) of each plate (20)
(P) Wire stitch (tying)
(I) Axillary lateral incisions
(T) Chest
(PR) "Pectus Carinatum" Proceeding
(AC) Superior and inferior costal arcs

DETAILED DESCRIPTION OF PREFERRED EMBODIMENT

The apparatus for the correction of chest wall deformities, such as "Pectus Carinatum", of the present invention, comprises essentially a bar (10) formed as a pressing element for correcting the congenital chest wall deformity, two plates (20) for stabilizing and fixing the bar (10), and threaded elements (30), particularly screws provided to form movable or removable attachments between said bar (10) and said plates (20), also allowing registration between the bar ends and the respective plates.

The bar (10) is preferably made from 316 L steel by cold lamination, though it may be made from various bio-compatible materials, such as titanium, cobalt-chrome, etc; bio-degradable materials of various kinds may also be used. The bar (10) is made following the specifications given by ASTM F382-95, having a minimum bending strength of about 65 in-lb or a minimum yield strength of the material of $35 \times 10^6$ psi or a minimum bending stiffness of about 1000 lb-in$^2$.

The bar (10) is a bar having a flattened, substantially rectangular, cross-section, with rounded edges, having an even thickness along its entire development, except for the opposing end portions of the bar. In these portions the bar (10) comprises respective similar planar grooves (11)(11'), having a wall thickness about half the thickness of the longitudinal section of said bar. The grooves (11)(11') are formed on one of the major faces of the bar (10), forming with said face respective steps (12)(12') in the form of a 45° chamfer. Said walls of grooves (11)(11') have a plurality passing holes (13)(13') aligned with their respective longitudinal axes (eb).

The bar (10) is provided in various sizes according to the requirements of each case, proposing, by way of example, lengths ranging from about 150 mm to about 425 mm with variations of about 25 mm between them; the bar width is about 12 mm, the thickness in the longitudinal section is about 3 mm and the thickness of the wall portions (11)(11') at the ends is about 1.5 mm.

Each stabilization and fixation plate (20) of the bar (10) is a rectangular piece having rounded corners and contour, made from the material mentioned above for bar (10). Each plate (20) is made from a piece having the same thickness as the bar (10) longitudinal section, having in its medium portion a straight groove or slot (21) extending transversely from side to side of the piece, defining two side portions (22) provided with peripheral holes (23) for fixation to the bone parts of the costal arcs. The groove or slot (21) is formed on one of the major faces of the piece (20), showing two steps (24), formed as a 45° chamfer, coupling the corresponding faces of the side portions (22). The groove or slot has a wall thickness the height of which is half the thickness of the plate and of the longitudinal section of bar (10). Considering the measures suggested previously for the bar (10), a wall thickness of about 3 mm in the portions (22) and a wall thickness in the groove or slot (21) of about 1.5 mm is proposed for plate (20). The length proposed for the plate (20) is about 50 mm and it arises from the costal arc (AC) separation; also, the width suggested is about 20 mm.

The slot (21), being provided to fit the tapered portion of the corresponding bar end (10), has a width and height consistent with said portion. On the slot (21) wall, attachment elements are formed that are cooperative with two consecutive holes (13) or (13') at the corresponding end portion of bar (10).

In the embodiment of this apparatus illustrated in FIGS. 1 to 4, side wall portions (22) of plate (20) have a pair of securing holes (23), formed adjacent said distal edges of said portions. Referring to this first embodiment of the invention, groove or slot wall (21) is provided with a pair of threaded holes (25) aligned to the medium longitudinal axis of said groove or slot and consistently separated from holes (13) or (13') of the corresponding bar end (10).

In this way, as portions (11)(11') of bar ends (10) are mounted on slots (21) of plates (20), the two threaded holes (25) may selectively match two consecutive holes (13) or (13') of the corresponding bar end. The bar ends (10) and the plates (20) are secured by screws (30) forming respective removable attachments.

Figure 5:
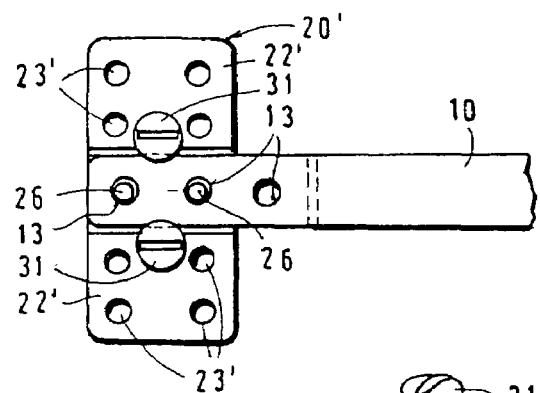
FIG. 5 is a plan view of the attachment between one of the bar ends and a respective fixation plate according to an embodiment variation of the invention.
Figure 6:
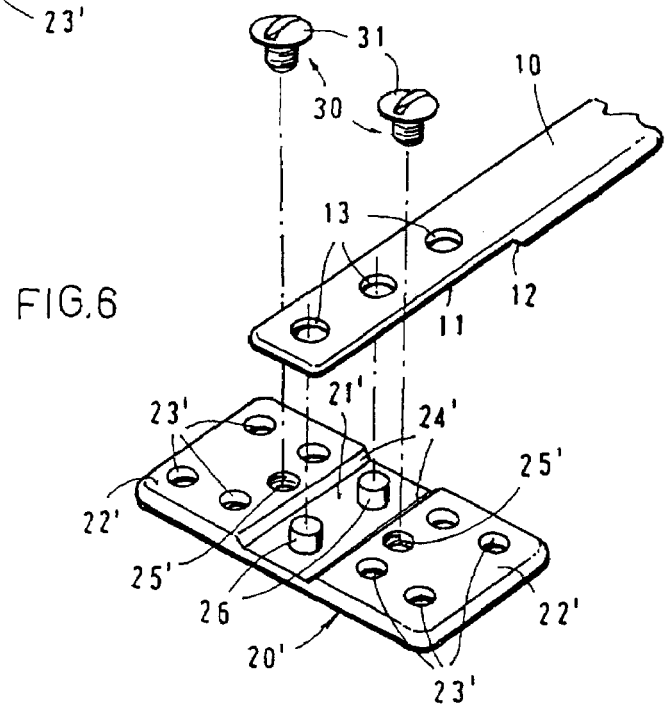
FIG. 6 is a perspective and exploded view of said attachment according to FIG. 5.
Figure 7:
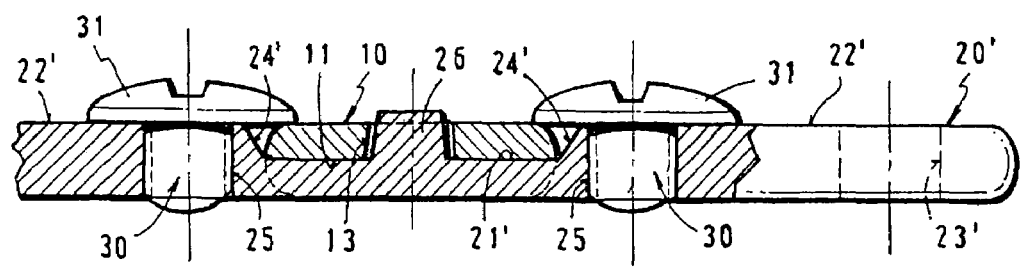
FIG. 7 is an enlarged partial and cross-sectional view of FIG. 5.

Referring to FIGS. 5 to 7, a variation of the embodiment of the improved apparatus is shown, specifically a variation for the bar (10) fixing plates. In this case, each plate (20') for stabilizing and securing the bar (10) is a rectangular piece with rounded corners and contour, made from the material mentioned above for bar (10). Each plate (20') is formed from a piece having the same thickness as the longitudinal section of bar (10), having in the medium portion a straight groove or slot (21') extending transversely from side to side of the piece, defining two side portions (22'). The groove or slot (21') is formed on each major face of plate (20'), showing two steps (24') formed as a 45° chamfer coupling the corresponding faces of side portions (22'). The groove or slot has a wall thickness the height of which is equal to half the thickness of the plate and of the longitudinal section of bar (10).

On the slot wall (21) two cylindrical projections (26) are formed that are aligned with the medium longitudinal axis of said groove or slot and consistently separated from holes (13) or (13') of the corresponding bar (10) end, which can selectively fit in two consecutive holes (13) or (13').

The side wall portions (22') of each plate (20') have four securing holes (23'), formed adjacent to said portion ends.

On the side wall portions (22'), adjacent to steps (24'), respective threaded holes (25') are formed to secure respective screws (30) the heads of which have contours that can be overlapped by the larger edges of the tapered portion (11) of the corresponding bar (10) end.

METHOD FOR CORRECTION OF "PECTUS CARINATUM"

The method for correction of the chest wall deformity called "Pectus Carinatum" comprises, according to our invention, the following steps:

Two small incisions (I) are initially made in the chest (T) axillary lateral region at the maximum proceeding height (PR). A pre-sternum tunnel is shaped just above the maximum proceeding. The elongated bar (10) is introduced, which has been previously shaped so that it will appropriately compress the chest deformity (PR) that usually has particular characteristics and which requires a particular shaping upon insertion. The procedure contemplates using a phleboextractor flexible metal element in order to pass a silk knot or a polyvinyl chloride tube (PVC) or the like through the subcutaneous tunnel. Through said tube, or by driving the knot, the passage of the compressing bar through said subcutaneous tunnel is made easy. Securing of the plates (20) is made by inserting the steel wire stitches (P) pericostally in the superior and inferior costal arcs (AC), so that each plate (20) is positioned perpendicular to the elongated bar (10) that is placed transversely between the left and right axillary regions. The pericostal stitches are fixed to the peripheral holes (23) of each plate (20). This embodiment is illustrated in FIGS. 8 to 11.

In another preferred embodiment of the inventive method, the fixation of the securing bar is made preferably in the posterior axillary region, in such location the costal arcs are curved and become vertical, so the fixation of said securing bar to the costal arcs is made easy and the perpendicular position of said securing bar vertically towards the compressing bar, which must keep a horizontal position towards the chest plane, at its attachment with the contralateral fixing plate, is made easy. In said posterior axillary location the fixing plate attached to the compressing bar by securing screws is covered by the wide dorsal muscle which provides a better esthetic result and avoids any kind of complications arising from the contact with the dermal elements. This preferred embodiment is illustrated in FIGS. 12 to 15.

Besides, it must be taken into account that eventual fixations of securing plates to one, two, three or more ribs as those described herein, or obvious variations thereof, through steel pericostal wire stitches must be considered as obvious variations from those described herein to support the method, the fixation to two ribs being that which provides the preferred embodiment for applying the apparatus on the costal arcs in the method described herein.

By externally compressing the sternum body the appropriate chest (T) contour is shaped, which is achieved by taking advantage of the chondrocostal elasticity and taking into account that, as the sternum-vertebral distance is reduced, an enlargement of the diameters of the base of both hemithorax occurs.

The sequential holes function to offer various fixation points in order to facilitate the fixation at the suitable point that best corrects the proceeding and in order to allow later regulations if the patient's chest stiffness makes it necessary or advisable to perform a two-stroke compression.

When appropriately fixing the securing bar and applying an intensive pressure on the compressing bar towards the patient's dorsum, it becomes difficult to place the securing screws as the screw pitch and the thread are tight-fitted.

For these purposes, the procedure contemplates the use of searching screws which are longer, larger and have tapered threaded point, which are initially placed in one of the threaded holes allowing to later place the securing screws in the second threaded hole, then removing the searching screw and placing the final securing screw in the first threaded hole.

The searching screws are also made of 316 L steel anticipating they must be definitely left as securing screws in cases in which their substitution for standard securing screws is impossible, or extremely difficult.

Besides the head of the searching screws as securing screws may be drilled and comprise one simple slot or two crossed slots, which provide a safe means for handling with the appropriate tool so as to secure it or unscrew it and remove it from its position.

The design of the fixing plate slot with angled edges facilitates its application and the contact between the fixing plate and the compressing bar when the perpendicular relation required by the attachment between both elements is not perfect.

An obvious comparison between the Nuss apparatus and method and the apparatus and method proposed herein, although they are used for different chest wall corrections, forces us to call attention to the fact that fixing the bar end of the Nuss apparatus with wire to a rib is neither reliable nor safe so as to stand the forces associated with the compressions made in the method proposed herein. Besides, the Nuss securing plate does not comprise pairs of holes that allow a wire stitch fixation to the ribs, while the arcuate slot of the securing plate and its distal hole are not secure either nor do they allow an appropriate fixation.

Subsequently, the muscle plane that is then covering the securing plate with the steel stitches surrounding the costal arcs is closed. If the suitable technique is used, there will be no gaps in the parietal pleura, thus preventing a pneumothorax. If this event does occur, either the affected hemithorax can be drained or it can be expanded by positive pressure of the anesthetic ventilation system and the gap can be closed by sutures, preventing a postoperative pneumothorax. Finally, the cellular tissue and the skin are closed. The patient's leaving hospital generally occurs 48 or 72 hours after surgery and there are no limitations to his usual activities given the firmness of the fixation system of the method that prevents the implant displacement.

The compressing bar contour applied to the ribs with the appropriate compression degree causes generally an appropriate immersion of said bar in the deep parietal planes. If a section of the compressing bar, by the action of the proceeding chondrocostal pressure causes compression on the dermal planes, it is advisable to apply massages on said region frequently in order to prevent adhesion of the superficial planes and its dermatological effects at said level. If bioabsorbable materials are used the prosthesis is not removed.

In the case of an implant by non-absorbable materials, the time it is kept varies and depends on the patient's age. The appropriate time in young patients in their growing period is considered that when said period stops.

In the case of adult patients, the apparatus must be kept for at least about two years. If the implant tolerance is good, an even longer time can be waited in order to insure that the appropriate chest contour is kept after the removal of the implant. The mode of removal comprises opening the lateral incisions, cutting and removing the wires surrounding the costal arcs, unscrewing the securing screws and removing the presternum bar by sliding it through the presternum channel by pulling from one of its ends.

Depending on the age and on the elasticity loss of the osteo-chondrocostal structures, a plurality of movements may be made that allow to reshape the anatomic contour:

percutaneous ostectomies on the costal arcs and in the sternum bone curved portion by drawing a line of bores with a punch, or by inserting a small sized chisel which leaves no dermal effects. The correction of frequent sternum base cartilage deformities and of the inferior costal arcs can be made without difficulties by small axillary lateral incisions (I) with or without use of videoscopic techniques. Sternum and chondral section ostectomies required in older patients can be made by these incisions (I) or by bilateral periareolar incisions.

Also in the cases in which Pectus Carinatum and Pectus Excavatum coexist, an intrathoracic retro-sternum bar can be implanted according to Nuss procedure, which is herein incorporated by reference, simultaneously or successively with the compression system implant, pre-sternally according to the current invention.

The materials and measures mentioned in the present invention for elements corresponding to the apparatus for performing chest wall deformity correction, which are also proposed to carry out the method for the correction of Pectus Carinatum, should not be considered as limitative of the scope of the invention, and they may be varied according to the characteristics of the deformity to be treated. Specifically in the case of bar (10), the use of only one or a greater number thereof may considered, in cases requiring a greater bending strength, a greater material yield strength or a greater bending stiffness. The procedure, when compressing and correcting the proceeding costal arc position, remarkably corrects the rotation of the vertebral bodies usually shown by these patients thus improving scolitic deformities.

Unexpectedly, it was found that this invention is also useful and safe for treating wall chest deformities such as "Pectus Excavatum" achieving a definite anchorage and effectively standing the forces and tensions that arise during the location of the apparatus in the patient and its later correcting stage preventing the bar complete turn that applies pressure, and that normally occurs in these cases during the two first postoperative months.

Thus, the apparatus of this invention is applicable for both kinds of deformities, i.e. both "Pectus Excavatum" and "Pectus Carinatum", comprising in its scope all the variations of "Pectus Carinatum" that normally occur, i.e. the apparatus is useful for correcting symmetrical and asymmetrical protrusions of the chest wall.

Various changes and variations of the apparatus for the correction of chest wall deformities, such as Pectus Carinatum, and of the method for the correction of Pectus Carinatum described according to the present invention will be obvious for those with ordinary knowledge of the art without departing from the scope and spirit of the invention. Although the invention has been described as related to a preferred specific embodiment and some variations thereof, it should be understood that the invention as it is claimed should be unduly limited to such specific embodiments. In fact, the various changes of the embodiment described to carry out the invention that are obvious for those with knowledge of the art, of the related fields, are intended to be included within the scope of the following claims.

The claims are a part of the description of the invention of this patent application.

The invention claimed is:

1. An apparatus for the correction of wall chest deformities such as "Pectus Carinatum", comprising a bar having a flattened cross-section, capable of being appropriately curved, the material being 316-L steel having minimum bending strength of about 65 in.lb, minimum yield strength of $35 \times 10^6$ psi and bending stiffness of about 1000 lbs.in$^2$, according to the values defined by ASTM F382-95, having two opposing ends associated to respective fixing plates provided in the medium portion of a receiving slot of the corresponding bar end and peripheral holes securing the bone parts of the costal arcs, wherein said bar and said fixing plates have substantially the same thickness, the bar end portions have the reduced thickness for respective planar grooves which consistently with the respective longitudinal axes have a plurality of regularly separated passing holes aligned therewith; and the fixing plates, being substantially rectangular, have in the respective slots cooperative attaching elements matching two consecutive holes on the tapered portion of the corresponding bar end, the wall thickness of each bar end portion and the wall thickness in the slot region of each plate having the same height, and said bar end portions and the respective fixing plates being linked by threaded elements, forming removable and axially registerable attachments.

2. An apparatus for the correction of chest wall deformities such as "Pectus Carinatum", according to claim 1, wherein said threaded elements are screws and said attaching elements of the slots are threaded holes aligned with the longitudinal axis of the flat slot faces whereon the bar and fixing plates are attached together.

3. An apparatus for the correction of chest wall deformities such as "Pectus Carinatum", according to claim 1, wherein the attachment elements between each plate and the tapered portion of the corresponding bar end are substantially cylindrical projections aligned with the longitudinal axis of the wall forming the slot and are fittingly and selectively related to two consecutive holes of the tapered portion of the corresponding bar end, and the threaded elements comprising at least two screws that are applied to respective threaded holes formed in the plate portions adjacent to the slot edges, said screws having head contours overlapping the greater edges of the tapered portion of the corresponding bar end.

4. A method for the correction of "Pectus Carinatum" using the apparatus according to any of the preceding claims, comprising the steps of:
   i) making two small incisions in the chest axillary lateral region at the maximum proceeding;
   ii) shaping a pre-sternum tunnel just above the maximum proceeding;
   iii) inserting the previously shaped, curved bar so that the concave face of said bar shall compress appropriately the chest deformity;
   iv) applying two fixing plates to the costal planes in perpendicular position between the longitudinal axes of said plates and the bar, and securing both plates pericostally;
   v) externally compressing the sternum body until the appropriate chest contour is shaped;
   vi) mounting the tapered portions of the bar ends on the slots of the respective plates; and
   vii) securing with screws said bar end portions and said plates.

5. A method for the correction of "Pectus Carinatum" according to claim 4, wherein the fixing plates are secured by pericostally inserting steel wire stitches in the bone parts of the superior and inferior costal arcs.

6. A method for the correction of "Pectus Carinatum" according to claim 4, wherein the bar fixing plates are secured by pericostally inserting steel wire stitches in the bone parts of the superior and inferior costal arcs in the posterior axillary region.

7. A method for the correction of "Pectus Carinatum" according to claim 4, wherein a plurality of movements is accessorily made allowing reshaping the anatomic contour.

8. A method for the correction of "Pectus Carinatum" according to claim 7, wherein the reshaping of the anatomic contour comprises making percutaneous ostectomies in the costal arcs and/or in the curved portion of the sternum bone.

9. A method for the correction of "Pectus Carinatum" according to claim 8, wherein once the correction of the chest wall deformity is achieved, the method further comprises the steps of:

viii) opening the lateral incisions;

ix) cutting and removing the wires surrounding the costal arcs;

x) unscrewing the securing screws; and xi) removing the plates and the pre-sternum bar.

* * * * *